United States Patent
Yang et al.

(12)

(10) Patent No.: US 6,730,292 B1
(45) Date of Patent: May 4, 2004

(54) HAIR CARE COMPOSITION COMPRISING A POLYPROPYLENE GLYCOL AND AN ESTER OIL

(75) Inventors: Jian-Zhong Yang, Kobe (JP); Ananthanarayan Venkateswaran, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/070,198

(22) PCT Filed: Sep. 3, 1999

(86) PCT No.: PCT/US99/20327

§ 371 (c)(1),
(2), (4) Date: Mar. 4, 2002

(87) PCT Pub. No.: WO01/17491

PCT Pub. Date: Mar. 15, 2001

(51) Int. Cl.[7] ................................................ A61K 7/075
(52) U.S. Cl. .................................. 424/70.11; 424/70.27
(58) Field of Search ............................ 424/70.11, 70.27

(56) References Cited

U.S. PATENT DOCUMENTS 5,916,548 A  *  6/1999  Hutchins et al. ......... 424/70.12

FOREIGN PATENT DOCUMENTS

| DE | 196 29 951 A | | 1/1998 |
|---|---|---|---|
| EP | 0 312 995 A | | 4/1989 |
| EP | 0 586 929 A | | 3/1994 |
| WO | WO-95 20939 A | | 8/1995 |
| WO | WO 98/24402 | * | 11/1998 |

* cited by examiner

*Primary Examiner*—Jyothsna Venkat
(74) *Attorney, Agent, or Firm*—Linda M. Sivik (57) ABSTRACT

Hair care compositions include a polypropylene glycol, an ester oil, and a gel matrix comprising a cationic surfactant, a solid fatty compound, and water. Hair care compositions also include a polypropylene glycol, an ester oil selected from a pentaerythritol ester oil, a trimethylol ester oil, and mixtures thereof, and a suitable carrier. The polypropylene glycol has a weight average molecular weight of from about 200 g/mol to about 100,000 g/mol. The HLB value of the ester oil is less than about 4.

2 Claims, 1 Drawing Sheet

HAIR CARE COMPOSITION COMPRISING A POLYPROPYLENE GLYCOL AND AN ESTER OIL

FIELD OF THE INVENTION

The present invention relates to a hair care composition. More specifically, the present invention relates to a hair care composition which provides a conditioning benefit.

BACKGROUND OF THE INVENTION

Human hair becomes soiled due to its contact with the surrounding environment and from sebum secreted by the scalp. The soiling of the hair causes it to have a dirty or greasy feel, and an unattractive appearance. The soiling of the hair necessitates shampooing with regularity.

Shampooing cleans the hair by removing excess soil and sebum. However, shampooing can leave hair in a wet, tangled, and generally unmanageable state. After shampooing, hair is often left in a dry, rough, lusterless, or frizzy condition due to removal of the hair's natural oils and other natural conditioning components. Furthermore, such hair may also suffer from a perceived loss of softness. In addition, hair may possess increased levels of static after drying, which can interfere with combing and reduce hair manageability. This results in a condition commonly referred to as "flyaway hair." Certain consumers consider such flyaway hair and the corresponding increase in total hair volume undesirable. Thus, it is desirable to provide smooth, soft, silky-feeling, and healthy-looking hair, while decreasing flyaway hair volume and total hair volume. In addition, it is typically desirable to increase the biodegradability of a hair care composition.

A variety of approaches have been developed to address these issues. Such approaches typically seek to increase smoothness, softness, and luster by including hair conditioning compounds, typically cationic compounds, such as catonic surfactants, into a hair care composition. Such hair conditioning compounds may also reduce static. In theory, these cationic compounds, including quaternary ammonium compounds, seek to neutralize the static charge on the hair, and thus reduce flyaway hair volume. However, these hair conditioning compounds do not sufficiently reduce total hair volume, and may be harsh on the hair, skin, or scalp.

Alternatively, oily compounds, such as a silicone, an ester oil, and/or a hydrocarbon oil have been included in hair care compositions to reduce flyaway hair. However, while these oily compounds may make hair feel smoother, more silky, and/or appear more lustrous, they are not sufficient to satisfy certain consumers.

Accordingly, the need remains for a hair care composition which noticeably reduces total hair volume and is easily biodegradable. The need also remains for a hair care composition which provides smoother, softer, more silky, and more lustrous hair. The need also remains for a hair care composition possessing these benefits, which is effectively deposited onto hair.

SUMMARY OF THE INVENTION

The present invention relates to a hair care composition which includes a polypropylene glycol, an ester oil, and a gel matrix. The polypropylene glycol has a weight average molecular weight of from about 200 g/mol to about 100,000 g/mol. The ester oil has the formula $R^1COOR^1$, wherein each $R^1$ is independently a $C_1$–$C_{22}$ alkyl, and the HLB value of the ester oil is less than about 4. The gel matrix includes a cationic surfactant, a solid fatty compound, and water.

In another aspect, the present invention relates to a hair care composition which includes a polypropylene glycol, an ester oil, and a suitable carrier. The polypropylene glycol has a weight average molecular weight of from about 200 g/mol to about 100,000 g/mol. The ester oil is selected from the group of pentaerythritol ester oils, trimethylol ester oils, and mixtures thereof, wherein the ester oil has an HLB value of less than about 4.

It has now been found that total hair volume is actually the sum of the "flyaway hair volume" and the "bulk hair volume." It has also been found that a measurable reduction of bulk hair area, flyaway hair area, and total hair area, by the Image Analysis Protocol described herein, corresponds to a noticeable decrease in the bulk hair volume, flyaway hair volume, and the total hair volume, respectively. Accordingly, it has been found that reducing the bulk hair area can therefore play a significant role in reducing the total hair volume. While certain compounds and compositions are known to reduce fly-away hair volume, for example, by reducing the static charge of hair, these compositions do not noticeably reduce bulk hair volume. It has now been found that a hair care composition which moisturizes the hair may noticeably reduce bulk hair volume, and may also noticeably reduce flyaway hair volume. This, in turn, provides a significant, noticeable reduction in total hair volume.

It has now been found that a hair care composition, preferably a hair conditioning composition, and/or a styling composition, containing a polypropylene glycol, an ester oil, and a suitable carrier may also more effectively deposit onto hair, and provide significant consumer-desirable benefits, such as an improved look and feel for hair, reduced bulk hair volume, reduced flyaway hair volume, and reduced total hair volume. Furthermore, the hair care composition is inexpensive to formulate, easily biodegradable, and possesses a non-oily feel.

These and other features, aspects, advantages, and variations of the present invention, and the embodiments described herein, will become evident to those skilled in the art from a reading of the present disclosure with the appended claims, and are covered within the scope of these claims.

BRIEF DESCRIPTION OF THE FIGURE

While the specification concludes with claims particularly pointing out and distinctly claiming the invention, it is believed that the invention will be better understood from the following description of the accompanying figure in which:

DETAILED DESCRIPTION OF THE INVENTION

All percentages, ratios and proportions herein are by weight of the final hair care composition, unless otherwise specified. All molecular weights herein are weight average molecular weights, unless otherwise specified. All temperatures are in degrees Celsius (°C.) unless otherwise specified. All documents cited are incorporated herein by reference in their entireties. Citation of any reference is not an admission regarding any determination as to its availability as prior art to the claimed invention. The drawing herein is not necessarily drawn to scale.

As used herein, the term "alkyl" means a hydrocarbyl moiety which is straight, branched, or cyclic, saturated or unsaturated. Unless otherwise specified, alkyl moieties are preferably saturated or unsaturated with double bonds, preferably with one or two double bonds. Included in the term "alkyl" is the alkyl portion of acyl groups.

As used herein, the term hair conditioning benefit indicates a conditioning, softening, bulk hair volume reduction, flyaway hair volume reduction, total hair volume reduction, moisturizing, improved wethair or dry-hair feel, lubricating, smoothening, softening, and/or other effect when applied to hair. All reductions in bulk hair volume, flyaway hair volume, and/or total hair volume are according to the Image Analysis Protocol, as described herein.

As used herein, the term "water-insoluble" means the compound is substantially not soluble in water at 25° C., when the compound is mixed with water at a concentration by weight of above 1.0%, preferably at above 0.5%, the compound is temporarily dispersed to form an unstable colloid in water, then is quickly separated from water into two phases.

Polypropylene Glycol

The hair care composition of the present invention contains a polypropylene glycol having a weight average molecular weight of from about 200 g/mol to about 100,000 g/mol, preferably from about 1,000 g/mol to about 60,000 g/mol. Without intending to be limited by theory, it is believed that the polypropylene glycol herein deposits onto, or is absorbed into hair to act as a humectant/moisturizer, and/or provides one or more other desirable hair conditioning benefits. As used herein, the term "polypropylene glycol" includes single-polypropylene glycol-chain segment polymers, and multi-polypropylene glycol-chain segment polymers. The general structure of branched polymers such as the multi-polypropylene glycol-chain segment polymers herein are described, for example, in "Principles of Polymerization," pp. 17–19, G. Odian, (John Wiley & Sons, Inc., 3$^{rd}$ ed., 1991).

The polypropylene glycol herein are typically polydisperse polymers. The polypropylene glycols useful herein have a polydispersity of from about 1 to about 2.5, preferably from about 1 to about 2, and more preferably from about 1 to about 1.5. As used herein, the term "polydispersity" indicates the degree of the molecular weight distribution of the polymer sample. Specifically, the polydispersity is a ratio, greater than 1, equal to the weight average molecular weight divided by the number average molecular weight. For a further discussion about polydispersity, see "Principles of Polymerization," pp. 20–24, G. Odian, (John Wiley & Sons, Inc., 3$^{rd}$ ed., 1991).

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. The solubility in water of the polypropylene glycol herein may be chosen by the artisan according to a variety of factors. A water-soluble polypropylene glycol is especially useful in, for example, a leave-on product. Without intending to be limited by theory, it is believed that such a water-soluble polypropylene glycol may possess many advantages in such a product. For example, such a polypropylene glycol may be easy to formulate, inexpensive, highly biodegradable, and easily obtainable. Accordingly, for a leave-on hair care composition, it is preferred that the polypropylene glycol herein be a water-soluble polypropylene glycol. Solubility information is readily available from polypropylene glycol suppliers, such as Sanyo Kasei (Osaka, Japan).

However, the present invention may also take the form of a rinse-off hair care composition. Without intending to be limited by theory, it is believed that in such a composition, a water-soluble polypropylene glycol may be too easily washed away before it effectively deposits on hair and provides the desired benefit(s). For such a composition, a less soluble, or even a water-insoluble polypropylene glycol is therefore preferred. Accordingly, for a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

The polypropylene glycol is typically present at a level of from about 0.5% to about 10%, and preferably from about 2% to about 6%, by weight of the hair care composition.

Preferably the polypropylene glycol is selected from the group consisting of a single-polypropylene glycol-chain segment polymer, a multi-polypropylene glycol-chain segment polymer, and mixtures thereof, more preferably selected from the group consisting of a single-polypropylene glycol-chain segment polymer of Formula I, below, a multi-polypropylene glycol-chain segment polymer of Formula II, below, and mixtures thereof. Without intending to be limited by theory, it is believed that these polypropylene glycols provide a good balance between performance, availability, biodegradability, and cost.

Single-Polypropylene Glycol-Chain Segment Polymer

Accordingly, a highly preferred single-polypropylene glycol-chain segment polymer has the formula:

$$HO—(C_3H_6O)_aH \qquad \text{(Formula I)},$$

wherein a is a value from about 4 to about 400, preferably from about 20 to about 100, and more preferably from about 20 to about 40.

The single-polypropylene glycol-chain segment polymer useful herein is typically inexpensive, and is readily available from, for example, Sanyo Kasei (Osaka, Japan), Dow Chemicals (Midland, Mich., USA), Calgon Chemical, Inc. (Skokie, Ill., USA), Arco Chemical Co. (Newton Square Pa., USA), Witco Chemicals Corp. (Greenwich, Conn., USA), and PPG Specialty Chemicals (Gumee, Ill., USA).

Without intending to be limited by theory, it is believed that once it has deposited onto a strand of hair, the shape and relatively small size of the single-polypropylene glycol-chain segment polymer herein allows it to easily penetrate the hair. While useful for both a leave-on and a rinse-off form, a single-polypropylene glycol-chain segment polymer is especially preferred if the hair care composition is to take a leave-on form. Furthermore, the multiple propylene oxide groups attract and maintain a significant amount of water to the hair so as to impart significant moisturization properties. This increased moisturization results in reduced flyaway hair volume, reduced bulk hair volume, and/or increases the manageability of the hair.

Multi-Polypropylene Glycol-Chain Segment Polymer

A highly preferred multi-polypropylene glycol-chain segment polymer has the formula:

(Formula II), wherein n is a value from about 0 to about 10, preferably from about 0 to about 7, and more preferably from about 1 to about 4. In Formula II, each R is independently selected from the group consisting of H, and $C_1$–$C_{30}$ alkyl, and preferably each R is independently selected from the group consisting of H, and $C_1$–$C_4$ alkyl. In Formula II, each b is independently a value from about 0 to about 2, preferably from about 0 to about 1, and more preferably b=0. Similarly, c and d are independently a value from about 0 to about 2, preferably from about 0 to about 1. However, the total of b+c+d is at least about 2, preferably the total of b+c+d is from about 2 to about 3. Each e is independently a value of 0 or 1, if n is from about 1 to about 4, then e is preferably equal to 1. Also in Formula II, x, y, and z is independently a value of from about 1 to about 120, preferably from about 7 to about 100, and more preferably from about 7 to about 100, where x+y+z is greater than about 20.

Examples of the multi-polypropylene glycol-chain segment polymer of Formula II which is especially useful herein includes polyoxypropylene glyceryl ether (n=1, R=H, b=0, c and d=1, e=1, and x, y, and z independently indicate the degree of polymerization of their respective polypropylene glycol-chain segments; available as New Pol GP-4000, from Sanyo Kasei, Osaka, Japan), polypropylene trimethylol propane (n=1, R=$C_2H_5$, b=1, c and d=1, e=1, and x, y, and z independently indicate the degree of polymerization of their respective polypropylene glycol-chain segments), polyoxypropylene sorbitol (n=4, each R=H, b=0, c and d=1, each e=1, and y, z, and each x independently indicate the degree of polymerization of their respective polypropylene glycol-chain segments; available as New Pol SP4000, from Sanyo Kasei, Osaka, Japan), and PPG-10 butanediol (n=0, c and d=2, and y+z=10; available as Probutyl DB-10, from Croda, Inc., of Parsippany, N.J., U.S.A.).

In a preferred embodiment, one or more of the propylene repeating groups in the polypropylene glycol is an isopropyl oxide repeating group. More preferably one or more of the propylene oxide repeating groups of the polypropylene glycol of Formula I and/or the polypropylene glycol of Formula II is an isopropyl oxide repeating group. Even more preferably, substantially all of the propylene oxide repeating groups of the polypropylene glycol of Formula I and/or the polypropylene glycol of Formula II are isopropyl oxide repeating groups. Accordingly, a highly preferred single-polypropylene glycol-chain segment polymer has the formula:

(Formula III), wherein a is defined as described above for Formula I. Similarly, a highly preferred multi-polypropylene glycol-chain segment polymer has the formula:

(Formula IV), wherein n, R, b, c, d, e, x, y, and z are defined as above, for Formula II. It is recognized that the isopropyl oxide repeating groups may also correspond to:

either alone, or in combination with the isomer depicted in Formula IV.

Ester Oil

The hair care composition of the present invention also contains an ester oil therein. The ester oil useful herein is of the formula:

$$R^1COOR^1 \qquad \text{(Formula V)},$$

wherein each $R^1$ is independently a $C_1$–$C_{22}$ alkyl, and preferably at least one $R^1$ is a $C_8$–$C_{22}$ alkyl. Each $R^1$ may be either a straight or branched alkyl chain. If $R^1$ is branched, it is preferred that $R^1$ have from 2 to 4 branches. The HLB value of the ester oil is less than about 4, preferably from about 0 to about 3. The ester oil useful herein should be easy to formulate, and process. Accordingly, the ester oil typically has a melting point of less than about 40° C., and is preferably water-insoluble, and in a liquid form at 25° C.

The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the alkyl alkoxylate may be found in tables and charts known in the art, or may be calculated with the following general equation: HLB=7+Σ(hydrophobic group values)+Σ(hydrophilic group values). The HLB and methods for calculating the HLB of a compound are explained in detail in "Surfactant Science Series, Vol. 1: Nonionic Surfactants", pp. 606–13, M. J. Schick (Marcel Dekker, Inc., New York, 1966).

Unless otherwise noted herein, the ester oils useful herein have a weight average molecular weight of greater than about 70 g/mol, preferably from about 100 g/mol to about 2,000 g/mol, and more preferably from about 160 g/mol to about 1,200 g/mol are especially useful herein. The preferred ester oil useful herein includes pentaerythritol ester oils, trimethylol ester oils, citrate ester oils, glyceryl ester oils, and mixtures thereof.

Without intending to be limited by theory, it is believed that ester oils efficiently deliver the polypropylene glycol to the hair, reduce flyaway hair volume, and/or provide other hair conditioning benefits. Furthermore, the ester oil herein provides moisturized feel, smooth feel, and manageability control to the hair when the hair is dried, yet does not leave the hair feeling greasy. Thus, with the addition of the ester oil, a composition is obtained which may provide particu- larly suitable conditioning benefits both when the hair is wet and also after it has dried. The ester oil may be included at a level of from about 0.5% to about 20%, preferably from about 2% to about 10%, and more preferably from about 3% to about 7% by weight of the composition.

Pentaerythritol ester oils useful herein are those of the following formula having a weight average molecular weight of at least 800 g/mol:

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the weight average molecular weight of the compound is from about 800 g/mol to about 1,200 g/mol.

Trimethylol ester oils useful herein are those of the following formula having a weight average molecular weight of at least 800 g/mol:

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the weight average molecular weight of the compound is from about 800 g/mol to about 1,200 g/mol.

Particularly preferable ester oils are pentaester oils and trimethylol ester oils, and more preferably pentaerythritol tetraisostearate, pentaerythritol tetraoleate, trimethylolpropane triisostearate, trimethylolpropane trioleate, and mixtures thereof. Such compounds are available from Kdkyo Alcohol (Japan) with the tradenames KAK P.T.I., and KAK T.T.I, and Shin-nihon Rika (Tokyo, Japan) with the tradenames PTO, and ENUJERUBU TP3SO.

Citrate ester oils useful herein are those having a weight average molecular weight of at least about 500 g/mol having the following formula:

wherein $R^{21}$ is OH or $CH_3COO$, and $R^{22}$, $R^{23}$, and $R^{24}$, independently, are branched, straight, saturated, or unsaturated alkyl aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl aryl, and alkylaryl groups having from 8 to about 22 carbons. More preferably, $R^{21}$, $R^{22}$, $R^{23}$ and $R^{24}$ are defined so that the weight average molecular weight of the compound is at least about 800 g/mol. Particularly useful citrate ester oils herein include triisocetyl citrate with tradename CITMOL 316 available from Bemel, triisostearyl citrate with tradename PELEMOL TISC available from Phoenix, and trioctyldodecyl citrate with tradename CITMOL 320 available from Bemel.

Glyceryl ester oils useful herein are those having a weight average molecular weight of at least about 400 g/mol and having the following formula:

wherein $R^{41}$, $R^{42}$, and $R^{43}$, independently, are branched, straight, saturated, or unsaturated alkyl, aryl, and alkylaryl groups having from 1 to about 30 carbons. Preferably, $R^{41}$, $R^{42}$, and $R^{43}$, independently, are branched, straight, saturated, or unsaturated alkyl, aryl, and alkylaryl groups having from 8 to about 22 carbons. More preferably, $R^{41}$, $R^{42}$, and $R^{43}$ are defined so that the weight average molecular weight of the compound is at least about 500 g/mol.

Particularly useful glyceryl ester oils herein include caprylic/capric triglyceride with the tradename Miglyol812, from Degussa-Hüls A G (Frankfurt, Germany), triisostearin with tradename SUN ESPOL G-318 available from Taiyo Kagaku, triolein with tradename CITHROL GTO available from Croda, Inc. (Parsippany, N.J., USA), trilinolein with tradename EFADERMA-F available from Vevy (Genova, Italy), or tradename EFA-GLYCERIDES from Brooks (South Plainfield, N.J., USA).

SUITABLE CARRIER

In an embodiment of the present invention, a hair care composition contains an ester oil selected from a pentaerythritol ester oil, a trimethylol ester oils, and mixtures thereof, a polypropylene glycol, and a suitable carrier. The suitable carrier contains a continuous phase, which is typically either water, or oil. The continuous phase is preferably water, but even a water continuous phase may also contain an oil emulsified, or dispersed therein, and visa-versa. Other carrier ingredients and/or other additional components may also be added into the suitable carrier. Without intending to be limited by theory, it is believed that pentaerythritol ester oils, trimethylol ester oils, and mixtures thereof deposit especially well onto hair when included in a suitable carrier, such as an aqueous carrier. It is believed that their combination of bulkiness, branching, and high molecular weight contribute significantly to their deposition and effectiveness, even in the absence of a gel matrix. Thus, while a gel matrix is preferred, these ester oils provide significant, desirable benefits, even in the absence of a gel matrix.

In another embodiment of the present invention, a hair care composition contains an ester oil according to Formula V, a polypropylene glycol, and a gel matrix. Without intending to be limited by theory, it is believed that for the ester oils of Formula V, a gel matrix significantly improves deposition and effectiveness.

1. Water

The final hair care composition of the present invention typically comprises at least about 60%, preferably at least about 70% water, and more preferably from about 75% to about 95% water. Deionized water is preferably used. Water from natural sources including mineral cations may also be used, depending on the desired characteristic of the product. The level and species of the suitable carrier are selected according to the compatibility with other components, and other desired characteristics of the product.

The suitable carrier may also include therein a lower alkyl alcohol, a polyhydric alcohol, and a mixture thereof. Lower alkyl alcohols useful herein are monohydric alcohols having 1 to 6 carbons, more preferably ethanol and isopropanol. The preferred polyhydric alcohols useful herein include propylene glycol, hexylene glycol, glycerin, and propane diol.

In a preferred embodiment, the suitable carrier is in the form of a gel matrix containing a cationic surfactant, a solid fatty alcohol, and water, and is typically characterized by a high viscosity of from about 5,000 cps to about 40,000 cps, preferably from about 10,000 cps to about 30,000 cps, and more preferably from about 12,000 cps to about 28,000 cps, as measured at 25° C., by means of a Brookfield Viscometer at shear rate of 1.0 rpm. If present, the gel matrix comprises from about 60% to about 99% preferably from about 70% to about 95%, and more preferably from about 80% to about 95%, by weight of the hair care composition.

In a highly preferred embodiment, the gel matrix is preferably a lamellar gel matrix, which provides improved deposition, wet hair feel, softness, and other substantial benefits. In a lamellar gel matrix, the weight ratio of cationic surfactant to solid fatty compound is from about 1:1 to about 1:20, preferably from about 1:2 to about 1:10, and more preferably form about 1:3 to 1:5. Generally, the preferred cationic surfactants in the lamellar gel matrix contain one or two long chain (e.g., $C_{12-30}$) alkyl groups, and a tertiary or quaternary amine group. Tertiary amine groups having one or two $C_{16-22}$ alkyl chains are preferred.

The existence of a lamellar gel matrix may be detected by differential scanning calorimetry (hereinafter referred to as "DSC") measurement of the composition. A profile chart obtained by DSC measurement describes chemical and physical changes of the scanned sample that involve an enthalpy change or energy gradient when the temperature of the sample is fluctuated. As such, the phase behavior and interaction among components of hair conditioning compositions of the present invention may be understood by their DSC profiles. DSC measurement of compositions of the present invention may be conducted by any suitable instrument available. For example, DSC measurement may be suitably conducted by Seiko DSC 6000 instrument available from Seiko Instruments Inc. In a typical measurement procedure, a sample is prepared by sealing an appropriate amount of the composition into a container made for DSC measurement and sealed. The weight of the sample is recorded. A blank sample i.e.; an unsealed sample of the same container is also prepared. The sample and blank sample are placed inside the instrument, and run under a measurement condition of from about −50° C. to about 130° C. at a heating rate of from about 1° C./minute to about 10° C./minute. The area of the peaks as identified are calculated and divided by the weight of the sample to obtain the enthalpy change in mJ/mg.

In a preferred lamellar gel matrix, the DSC profile shows a formation peak of larger than about 3 mJ/mg. The position of the peaks are identified by the peak top position. The DSC profile of the preferred lamellar gel matrix shows a single peak having a peak top temperature of from about 55° C. to about 75° C., and from about 6 mJ/mg to about 10 mJ/mg, and no peaks larger than 3 mJ/mg from 40° C. to 55° C. It is believed that a composition formed predominantly with such a lamellar gel matrix shows a relatively stable phase behavior during the temperature range of from about 40° C. to about 55° C. In an even more preferred lamellar gel matrix, the DSC profile shows a single peak having a peak top temperature of about 69° C., at about 8 mJ/mg, and no peaks larger than 3 mJ/mg from 40° C. to about 65° C.

a. Cationic Surfactant

Among the cationic surfactants useful herein are those corresponding to the general Formula (I):

wherein at least one of $R^{101}$, $R^{102}$, $R^{103}$ and $R^{104}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{101}$, $R^{102}$, $R^{103}$ and $R^{104}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and $X^-$ is a salt-forming anion such as those selected from halogen (e.g., chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{101}$, $R^{102}$, $R^{103}$ and $R^{104}$ are independently selected from $C_1$ to about $C_{22}$ alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general Formula (I), preferred are those containing in the molecule at least one alkyl chain having at least 16 carbons. Nonlimiting examples of such preferred cationic surfactants include: behenyl trimethyl ammonium chloride available, for example, with tradename INCROQUAT TMC-80 from and ECONOL TM22 from Sanyo Kasei (Osaka, Japan); cetyl trimethyl ammonium chloride available, for example, with tradename CA-2350 from Nikko Chemical (Tokyo, Japan), hydrogenated tallow alkyl trimethyl ammonium chloride, dialkyl (14–18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl(myristylacetate)ammonium chloride, and N-(stearoyl colamino formyl methyl)pyridinium chloride.

Also preferred as cationic surfactants are hydrophilically substituted cationic surfactants in which at least one of the substituents contain one or more aromatic, ether, ester, amido, or amino moieties present as substituents or as linkages in the radical chain, wherein at least one of the $R^{101}$–$R^{104}$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic surfactant contains from 2 to about 10 nonionic hydrophile moieties located within the above stated ranges. Preferred hydrophilically substituted cationic surfactants include those of Formulas (II) through (VII) below:

(II)

wherein $n^1$ is from 8 to about 28, $m^1+m^2$ is from 2 to about 40, $Z^1$ is a short chain alkyl, preferably a $C_1$–$C_3$ alkyl, more preferably methyl, or $(CH_2CH_2O)_{m3}H$ wherein $m^1+m^2+m^3$ is up to 60, and $X^-$ is a salt-forming anion as defined above;

(III)

wherein $n^2$ is 1 to 5, one or more of $R^{105}$, $R^{106}$, and $R^{107}$ are independently an $C_1$–$C_{30}$ alkyl, the remainder are $CH_2CH_2OH$, one or two of $R^{108}$, $R^{109}$, and $R^{110}$ are independently an $C_1$–$C_{30}$ alkyl, and remainder are $CH_2CH_2OH$, and $X^-$ is a salt-forming anion as mentioned above;

(IV)

(V)

wherein, independently for formulas (IV) and (V), $Z^2$ is an alkyl, preferably $C_1$–$C_3$ alkyl, more preferably methyl, and $Z^3$ is a short chain hydroxyalkyl, preferably hydroxymethyl or hydroxyethyl, $n^3$ and $n^4$ independently are integers from 2 to 4, inclusive, preferably from 2 to 3, inclusive, more preferably 2, $R^{111}$ and $R^{112}$, independently, are substituted or unsubstituted hydrocarbyls, $C_{12}$–$C_{20}$ alkyl or alkenyl, and $X^-$ is a salt-forming anion as defined above;

(VI)

wherein $R^{113}$ is a hydrocarbyl, preferably a $C_1$–$C_3$ alkyl, more preferably methyl, $Z^4$ and $Z^5$ are, independently, short chain hydrocarbyls, preferably $C_2$–$C_4$ alkyl or alkenyl, more preferably ethyl, $m^4$ is from 2 to about 40, preferably from about 7 to about 30, and $X^-$ is a salt-forming anion as defined above;

(VII)

wherein $R^{114}$ and $R^{115}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and $X^-$ is a salt-forming anion as defined above;

(VIII)

wherein $n^5$ is 2 or 3, $R^{116}$ and $R^{117}$, independently are $C_1$–$C_3$ hydrocarbyls preferably methyl, and $X^-$ is a salt-forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemicals (Greenwich, Conn., USA), MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel (Germany), and ATLAS G265 from ICI Americas (Wilmington, Del., USA).

Salts of primary, secondary, and tertiary fatty amines are also suitable catonic surfactants. The alkyl groups of such amines preferably have from about 12 to about 22 carbon atoms, and can be substituted or unsubstituted. Particularly useful are amido substituted tertiary fatty amines. Such amines, useful herein, include stearamidopropyldimethylamine, stearamidopropyldimethylamine, stearamidoethyldiethylamine, stearamidoethyldimethylamine, palmitamidopropyldimethylamine, palmitamidopmpyldiethylamine, palmitamidoethyldiethylamine, palmitamidoethyldiethylamine, behenamidopropyldimethylamine, behenamidopropyldimethylamine, behenamidoethyldiethylamine, behenamidoethyldiethylamine, arachidamidopropyldimethylamine, arachidamidopropyldimethylamine, arachidamidoethyldiethylamine, arachidamidoethyldiethylamine, dimethylaminoethylacrylamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to H$^+$ from the acid is preferably from about 1:0.3 to 1:1.2, and more preferably from about 1:0.5 to about 1:1.1.

b. Solid Fatty Compound

The solid fatty compound useful herein has a melting point of 25° C. or higher, and is selected from the group consisting of fatty alcohols, fatty acids, and mixtures thereof. It is understood by the artisan that the compounds disclosed in this section of the specification can in some instances fall into more than one classification, e.g., some fatty alcohol derivatives may also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The solid fatty compound is included in the composition at a level by weight of from about 0.1% to about 20%, preferably from about 1% to about 15%, more preferably from about 2% to about 10%.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

Solid fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity may provide good rinsability from the hair when the consumer rinses off the composition.

Commercially available solid fatty compounds useful herein include: cetyl alcohol, stearyl alcohol, and behenyl alcohol having tradenames KONOL series available from Shin-nihon Rika (Osaka, Japan), and NAA series available from NOF (Tokyo, Japan); pure behenyl alcohol having tradename 1-DOCOSANOL available from Wako Chemical (Osaka, Japan), various fatty acids having tradenames NEO-FAT available from Akzo (Chicago, Ill., USA), HYSTRENE available from Witco Corp. (Dublin, Ohio, USA), and DERMA available from Vevy (Genova, Italy).

While poly fatty alcohols may form the gel matrix, mono fatty alcohols are preferred. Either the cationic surfactant, and/or the solid fatty compound may be first mixed with, suspended in, and/or dissolved in water when forming a gel matrix.

2. Oil

In addition to the ester oil described above, an oil, having a melting point of less than about 25° C., may also be useful herein. These oils may provide conditioning benefits such as softness and flexibility to the hair. Nonlimiting examples of the oils useful herein are found in International Cosmetic Ingredient Dictionary, Fifth Edition, 1993, and CTFA Cosmetic Ingredient Handbook, Second Edition, 1992.

In a preferred embodiment containing an alkyl alkoxylate (described below), an oil is also present. It has now been found that when present, an alkyl alkoxylates may undesirably migrate to the aqueous phase, suffer from stability issues, and/or possess inadequate deposition efficiency when included by themselves in an aqueous carrier. Without intending to be limited by theory, it is believed that these stability problems arise from solubility differences between the typical production temperature and the typical storage temperature, chemical degradation of the oil-miscible agent, etc. In certain cases, it is believed that a phase change in-and-of-itself may affect stability and/or deposition efficiency. For example, the alkyl alkoxylates described herein may be more water-soluble at lower temperatures (e.g., storage temperatures), than at higher temperatures (e.g., production temperatures). If such an alkyl alkoxylate enters the aqueous phase from the oil-phase, its deposition efficiency onto hair may be significantly reduced. In such a case, even though it is not degraded or otherwise chemically altered, the alkyl alkoxylate may not efficiently deposit on the hair, because it is too easily washed away during use. Such a low deposition efficiency is undesirable.

Thus, it has now been found that stability and deposition efficiency of certain alkyl alkoxylates may decrease as they migrate from one phase to the other over time (e.g., during storage, transport, etc.). Thus, such a phase change may result in a significant decrease in the overall performance of the composition. It is therefore desirable to minimize such undesirable phase changes. Accordingly, in a preferred embodiment, the suitable carrier comprises an oil having an HLB value of from about 0 to about 3, preferably from about 0 to about 2, and more preferably from about 0 to about 1. Without intending to be limited by theory, it is believed that such oils tend to have an affinity for hair, and thus easily deposit thereupon. As noted, the preferred alkyl alkoxylate is miscible in oil. Thus, when mixed with this alkyl alkoxylate prior to its addition to the suitable carrier, the oil may entrap the alkyl alkoxylate therein. Furthermore, the low HLB value of these oils provides a highly hydrophobic environment which reduces the likelihood that the alkyl alkoxylate will undergo a phase change during storage. This in turn enhances the alkyl alkoxylate's stability during storage, and prevents it from easily washing away during, for example, rinsing of the hair. Thus, such an oil is especially preferred in a rinse-off hair conditioning composition, or a hair shampoo composition. In addition to entrapping the alkyl alkoxylate therein, these oils may also act as a carrier which itself further enhances actual deposition. Additionally, the oil may itself provide desirable benefits, such as improved combability, dry-hair feel, shininess, softness, smoothness, and/or slipperiness.

The oil useful herein is typically a liquid at room temperature, and therefore has a melting point below about 25° C. Preferred examples of the oil useful herein include liquid fatty alcohols and their derivatives, fatty acids and their derivatives, hydrocarbons, silicone compounds, and mixtures thereof which possess an HLB value of from about 0 to about 3, preferably from about 0 to about 2, and more preferably from about 0 to about 1. More preferred examples of the oil useful herein include fatty acid esters, liquid fatty alcohols, hydrocarbons, and mixtures thereof which possess the above HLB value. Even more preferred examples of the oil useful herein include liquid fatty alcohols such as oleyl alcohol, isostearyl alcohol, isocetyl alcohol and mixtures thereof which fall within the above HLB range.

Unless otherwise specifically noted, the oil may be included at a level of from about 0.1% to about 20%, preferably from about 0.5% to about 10%, more preferably from about 1% to about 5% by weight of the hair care composition.

a. Liquid Fatty Alcohol and Fatty Acid

The liquid fatty alcohols useful herein include those having from about 10 to about 30 carbon atoms, preferably from about 12 to about 22 carbon atoms, and more preferably from about 16 to about 22 carbon atoms. These liquid fatty alcohols maybe straight or branched chain alcohols and may be saturated or unsaturated alcohols, preferably unsaturated alcohols. Solid fatty compounds are those fatty alcohols which, when in their substantially pure forms, are solid at 25° C., while liquid fatty alcohols are those fatty alcohols which are liquid at 25° C. Nonlimiting examples of these compounds include oleyl alcohol, palmitoleic alcohol, isostearyl alcohol, isocetyl alcohol and mixtures thereof. While poly fatty alcohols are useful herein, mono fatty alcohols are preferred.

The fatty acids useful herein include those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, ethyl linolenic acid, arachidonic acid, and ricinolic acid.

The fatty acid derivatives and fatty alcohol derivatives are defined herein to include, for example, esters of fatty acids, alkoxylated fatty alcohols, alkyl ethers of fatty alcohols, alkyl ethers of alkoxylated fatty alcohols, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyldodecyl oleate, oleyl oleate, decyl oleate, butyl oleate, methyl oleate, octyldodecyl stearate, octyldodecyl isostearate, octyldodecyl isopalmitate, octyl isopelargonate, octyl pelargonate, hexyl isostearate, isopropyl isostearate, isodecyl isononanoate, isopropyl isostearate, ethyl isostearate, methyl isostearate and oleth-2.

Commercially available liquid fatty alcohols and their derivatives useful herein include: oleyl alcohol with tradename UNJECOL 90BHR available from Shin-nihon Rika, various liquid esters with tradenames SCHERCEMOL series available from Scher, and hexyl isostearate with a tradename HIS and isopropyl isostearate having a tradename ZPIS available from Kokyu Alcohol.

b. Hydrocarbon

The hydrocarbons useful herein include straight chain, cyclic, and branched chain hydrocarbons which can be either saturated or unsaturated, so long as they have a melting point of not more than about 25° C. These hydrocarbons have from about 12 to about 40 carbon atoms, preferably from about 12 to about 30 carbon atoms, and preferably from about 12 to about 22 carbon atoms. Also encompassed herein are polymeric hydrocarbons of alkenyl monomers, such as polymers of $C_{2-6}$ alkenyl monomers. These polymers can be straight or branched chain polymers. The straight chain polymers will typically be relatively short in length, having a total number of carbon atoms as described above. The branched chain polymers can have substantially higher chain lengths. The number average molecular weight of such materials can vary widely, but will typically be up to about 500 g/mol, preferably from about 200 g/mol to about 400 g/mol, and more preferably from about 300 g/mol to about 350 g/mol. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polyisobutene, and mixtures thereof. Preferred for use herein are hydrocarbons selected from the group consisting of mineral oil, poly α-olefin oils such as isododecane, isohexadecane, polybutene, polyisobutene, and mixtures thereof.

Poly α-olefin oils useful herein are those derived from 1-alkene monomers having from about 6 to about 16 carbons, preferably from about 6 to about 12 carbons atoms. Nonlimiting examples of 1-alkene monomers useful for preparing the poly α-olefin oils include 1-hexene, 1-octene, 1-decene, 1-dodecene, 1-tetradecene, 1-hexadecene, branched isomers such as 4-methyl-1-pentene, and mixtures thereof. Preferred 1-alkene monomers useful for preparing the poly α-olefin oils are 1-octene, 1-decene, 1-dodecene, 1-tetradecene, 1-hexadecene, and mixtures thereof. Poly α-olefin oils useful wherein further have a viscosity of from about 1 to about 35,000 cps, a weight average molecular weight of from about 200 g/mol to about 60,000 g/mol, and a polydispersity of no more than about 3.

Poly α-olefin oils having a weight average molecular weight of at least about 800 g/mol are useful herein, to provide long lasting moisturized feel to the hair. However, poly α-olefin oils having a weight average molecular weight of less than about 800 g/mol are also useful herein, to provide a smooth, light, clean feel to the hair. Particularly useful poly α-olefin oils herein include polydecenes with tradename PURESYN 6 having a weight average molecular weight of about 500 and PURESYN 100 having a weight average molecular weight of over 3000 g/mol available from Mobil Chemical Co.

Commercially available hydrocarbons useful herein include isododecane, isohexadecane, and isoeicosene with tradenames PERMETHYL 99A, PERMETHYL 101A, and PERMETHYL 1082, available from Presperse (South Plainfield N.J., USA), a copolymer of isobutene and normal butene with tradenames INDOPOL H-100 available from AmocoChemicals (Chicago Ill., USA), mineral oil with tradename BENOL available from Witco Chemicals, isoparaffin with tradename ISOPAR from Exxon Chemical Co. (Houston Tex., USA), and polydecene with tradename PURESYN 6 from Mobil Chemical Co.

The suitable carrier may also include therein solutions of lower alkyl alcohols and polyhydric alcohols. Lower alkyl alcohols useful herein are monohydric alcohols having 1 to 6 carbons, more preferably ethanol and isopropanol. The preferred polyhydric alcohols useful herein include propylene glycol, hexylene glycol, glycerin, and propane diol.

Alkyl Alkoxylate

The hair care composition preferably includes an alkyl alkoxylate therein. The alkyl alkoxylates useful herein may provide, for example, softening, conditioning, total hair volume reduction, flyaway hair volume reduction, bulk hair volume reduction, and/or other benefits. The alkyl alkoxylate useful herein has the formula: $R^3—O—(R^2—O)_nH$, wherein each $R^2$ is independently a $C_2$–$C_4$ alkyl group, preferably each $R^2$ is independently selected from the group consisting of a saturated $C_2H_4$ group, and a saturated $C_3H_6$ group, and more preferably each $R^2$ is independently selected from the group consisting of a saturated and linear $C_2H_4$ group, and a saturated and linear $C_3H_6$ group; wherein $R^3$ is an alkyl group having from about 1 to about 30 carbon atoms, preferably from about 6 to about 22 carbon atoms, and more preferably from about 8 to about 18 carbon atoms; $R^3$ may be branched or, linear, and saturated or unsaturated, but is preferably linear and saturated, or unsaturated having about one double bond;

n is a value from about 1 to about 10, preferably from about 2 to about 8, and more preferably from about 3 to about 6;

the weight average molecular weight of the alkyl alkoxylate is less than about 500 g/mol, preferably from about 100 to about 500 g/mol, and more preferably from about 200 to about 500 g/mol; and the HLB value of the alkyl alkoxylate is from about 5 to about 12, preferably from about 6 to about 11, and more preferably from about 6 to about 10.

As may be seen from the HLB values, such alkyl alkoxylates are miscible in both oil and water. Furthermore, such alkyl alkoxylates typically have a melting point of less than about 30° C., preferably less than about 25° C., and more preferably less than about 20° C., and have a cloud point (1% solution) of less than about 50° C., preferably less than about 40° C., and more preferably less than about 35° C.

Without intending to be limited by theory, it is believed that the alkyl alkoxylates useful herein provide a bulk hair volume reduction benefit by the following mechanism: The hydrophobic alkyl chains attach to hair fibers, even under rinse-off conditions, while the hydrophilic alkoxylate groups attract water molecules and bring them to the hair fibers. This moisturizes the hair fiber, and helps maintain it in a flexible, soft, and plastic state. This in turn, allows the hair fiber to maintain a well-aligned conformation (with respect to other hair fibers) and to easily recovery from deformation. This further increases the likelihood that the hair fibers will remain parallel, and/or hang straight down. This significantly reduces the space between the individual hair fibers, and therefore reduces bulk hair volume.

Without intending to be limited by theory, it is also believed that the alkyl alkoxylate may reduce flyaway hair volume as well. By moisturizing the hair fiber, the alkyl alkoxylate may also reduce the hair fiber's static charge and crookedness. This in turn, reduces the electrostatic repulsion and space between hair fibers, which leads to a reduction in flyaway volume.

From a cost, availability, and performance standpoint, alkyl ethoxylates are especially preferred alkyl alkoxylates useful herein, and include, for example, by CTFA name: oleth-5, oleth-3, steareth-5, steareth-4, ceteareth-5, ceteareth-4, and ceteareth-3, as well as mixtures of $C_{9-11}EO5$, mixtures of $C_{9-11}EO2.5$, mixtures of $C_{12-13}EO3$, mixtures of $C_{11-13}EO5$, and mixtures thereof. These alkyl ethoxylates are available from, for example, Croda, Inc., of Parsippany, N.J., U.S.A., Shell Chemical of U.S.A., BASF of Germany, Mitsubishi Chemical of Tokyo, Japan, and Nikko Chemical of Tokyo, Japan. Such alkyl ethoxylates are especially preferred for use in rinse-off hair conditioning compositions.

If present, the alkyl alkoxylate is provided in the hair care composition at a level of from about 0.1% to about 20%, preferably from about 0.2% to about 15%, and more preferably from about 0.5% to about 10%, by weight of the hair care composition. If the hair care composition is a rinse-off hair conditioning composition, then the alkyl alkoxylate is preferably present at a level of at least about 1%, more preferably from about 2% to about 20%, and even more preferably from about 3% to about 10%, by weight of the rinse-off hair conditioning composition.

If the hair care composition is intended for use as a rinse-off hair conditioning composition, it is highly preferred that the alkyl alkoxylate have a cloud point of less than about 40° C. Without intending to be limited by theory, it is believed that this significantly improves the deposition efficiency of the alkyl alkoxylate onto hair.

Other Additional Components

Certain other additional components are preferred in the present invention. These include, compounds which may provide, for example, an additional hair care, and/or hair conditioning benefit when included herein. Preferred other additional components include a silicone compound, a hydrophobically modified cellulose ether, a cationic conditioning compound, an anti-microbial agent, an herbal extract, and mixtures thereof. Unless otherwise noted, such other additional components generally are typically used individually at levels from about 0.001% to about 10.0%, preferably from about 0.01% to about 5.0% by weight of the composition.

1. Silicone Compound

The compositions of the present invention preferably contain a silicone compound. The silicone compounds useful herein include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by any suitable method known in the art, including emulsion polymerization. The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

The silicone compounds for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970. Silicone compounds of high molecular weight may be made by emulsion polymerization. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The silicone compound is preferably included in the composition at a level by weight from about 0.01% to about 20%, more preferably from about 0.05% to about 10%.

The silicone compounds herein also include polyalkyl or polyaryl siloxanes with the following structure (I)

(I)

wherein $R^{123}$ is alkyl or aryl, and x is an integer from about 7 to about 8,000. $Z^8$ represents groups which block the ends of the silicone chains. The alkyl or aryl groups substituted on the siloxane chain ($R^{123}$) or at the ends of the siloxane chains $Z^8$ can have any structure as long as the resulting silicone remains fluid at room temperature is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{123}$ groups on the silicon atom may represent the same group or different groups. Preferably, the two $R^{123}$ groups represent the same group. Suitable $R^{123}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispensability characteristics of the silicone. These material are also known as dimethicone copolyols.

Other silicone compounds include amino substituted materials. Suitable alkylamino substituted silicone compounds include those represented by the following structure (II)

(II)

wherein $R^{124}$ is H, $CH_3$ or OH, $p^1$, $p^2$, $q^1$ and $q^2$ are integers which depend on the molecular weight, the weight average molecular weight being approximately between 5,000 and 10,000. This polymer is also known as "amodimethicone".

Suitable amino substituted silicone fluids include those represented by the formula (III)

(III)

in which G is chosen from the group consisting of hydrogen, phenyl, OH, $C_1$–$C_6$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{125}$ is a monovalent radical of formula $C_{q3}H_{2q3}L$ in which $q^3$ is an integer from 2 to 8 and L is chosen from the groups

—N($R^{126}$)$CH_2$—$CH_2$—N($R^{126}$)$_2$

—N($R^{126}$)$_2$

—N($R^{126}$)$_3$X'

—N($R^{126}$)$CH_2$—$CH_2$—NR$^{126}$H$_2$X' in which $R^{126}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (III) is the polymer known as "trimethylsilylamodimethicone" wherein $R^{124}$ is $CH_3$.

Other amino substituted silicone polymers useful herein include cationic amino substituted silicones represented by the formula (V):

where $R^{128}$ denotes a monovalent hydrocarbon radical having from 1 to 18 carbon atoms, preferably an alkyl or alkenyl radical such as methyl; $R^{129}$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551 to Geen; U.S. Pat. No. 3,964,500 to Drakoff, issued Jun. 22, 1976; U.S. Pat. No. 4,364,837 to Pader, issued Dec. 21, 1982; and British Pat. No. 849,433 to Woolston. "Silicon Compounds" distributed by Petrarch Systems, Inc., 1984, provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer, et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a weight average molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional or di-functional, or bath, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

The method of manufacturing these silicone compounds, can be found in Encyclopedia of Polymer Science and Engineering, Volume 15, Second Edition, pp. 204–308, John Wiley & Sons, Inc., 1989.

Silicone materials and silicone resins in particular may conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.05}$; D denotes the difunctional unit $(CH_3)_2SiO$; T denotes the trifunctional unit $(CH_3)SiO_{1.5}$; and Q denotes the quadri- or tetra-functional unit SiO2. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with the weight average molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for used herein which are preferred are MQ, MT, MTQ, MQ and MDTQ resins. Thus, the preferred silicone substitu nt is methyl. Especially preferred are MQ resins wherein the M:Q ratio is from about 0.5:1.0 to about 1.5:1.0 and the weight average molecular weight of the resin is from about 1000 to about 10,000.

Commercially available silicone compounds which are useful herein include Dimethicone with tradename D-130, cetyl Dimethicone with tradename DC2502, stearyl Dimethicone with tradename DC2503, emulsified polydimethyl siloxanes with tradenames DC1664 and DC1784, and alkyl grafted copolymer silicone emulsion with tradename DC2-2845; all available from Dow Corning Corporation, and emulsion polymerized Dimethiconol available from Toshiba Silicone as described in GB application 2,303,857.

2. Hydrophobically Modified Cellulose Ether

It is preferred that the hair care composition contain therein from about 0.01% to about 2%, preferably from about 0.01% to about 1%, and more preferably from about 0.1% to about 0.5%, of a hydrophobically modified cellulose ether.

The hydrophobically modified cellulose ethers may provide an increase in bulk hair volume. When combined with the polypropylene glycol and ester oil of the present invention, the hydrophobically modified cellulose ethers may provide a balance between decreased flyaway hair, and increased bulk hair. The controlled level of hydrophobically modified cellulose ether also provides acceptable rheology profiles in the conditioning composition of this invention, so this composition provides satisfactory spreadability on the hair. The hydrophilic cellulose backbone has a weight average molecular weight of about less than 800,000 g/mol, preferably from about 20,000 g/mol to about 700,000 g/mol, and more preferably form about 50,000 g/mol to about 700,000 g/mol. Hydroxyethyl cellulose of this molecular weight is known to be one of the most hydrophilic of the materials contemplated. Thus, hydroxyethyl cellulose can be modified to a greater extent than other hydrophilic cellulose backbones.

The hydrophilic cellulose backbone is further substituted with a hydrophobic substitution group via an ether linkage to render the hydrophobically modified cellulose ether to have less than 1% water solubility, preferably less than 0.2% water solubility. The hydrophobic substitution group is selected from a straight or branched chain alkyl group of from about 10 to about 22 carbons; wherein the ratio of the hydrophilic groups in the hydrophilic cellulose backbone to the hydrophobic substitution group being from about 2:1 to about 1000:1, preferably from about 10:1 to about 100:1.

Commercially available hydrophobically modified cellulose ethers useful herein include: cetyl hydroxyethylcellulose having tradenames NATROSOL PLUS 330CS and POLYSURF 67, both available from Aqualon Company, Delaware, USA, having a cetyl group substitution of about 0.4% to about 0.65% by weight of the entire polymer.

3. Cationic Conditioning Compound

A cationic hair conditioning compound is preferred herein, and includes the cationic surfactants described above, cationic polymers, the cationic amino substituted silicones described above, and mixtures thereof. If present, the cationic hair conditioning compound is typically at a level of preferably from about 0.5% to about 5%, more preferably from about 1% to about 3% by weight of the composition.

The hair care compositions of the present invention may comprise one or more cationic polymers. As used herein, the term "polymer" includes materials whether made by polymerization of one type of monomer or made by two (i.e., copolymers) or more types of monomers. Preferably, the cationic polymer is a water-soluble cationic polymer. As used herein, the term "water-soluble" cationic polymer, indicates a polymer which is sufficiently soluble in water to form a substantially clear solution to the naked eye at a concentration of 0.1% in water (distilled or equivalent) at 25° C. The preferred cationic polymer will be sufficiently soluble to form a substantially clear solution at 0.5% concentration, more preferably at 1.0% concentration.

The cationic polymers herein will generally have a weight average molecular weight which is at least about 5,000, preferably from about 10,000 to about 10 million, more preferably, from about 100,000 to about 2 million. The cationic polymer will generally have cationic nitrogen-containing moieties such as quaternary ammonium or cationic amino moieties, and mixtures thereof.

The cationic nitrogen-containing moiety will be present generally as a substituent, on a fraction of the total monomer units of the cationic hair conditioning polymers. Thus, the cationic polymer may comprise copolymers, terpolymers, etc. of quaternary ammonium or cationic amine-substituted monomer units and other non-cationic units r ferred to herein as spacer monomer units. Such polymers are known in the art, and a variety may be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

The cationic charge density of the cationic polymer is preferably at least about 0.1 meq/gram, more preferably at least about 0.5 meq/gram, even more preferably at least about 1.1 meq/gram, and still more preferably at least about 1.2 meq/gram. Cationic charge density of the cationic polymer may be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterion may be utilized for the cationic polymers so long as the water solubility criteria is met. Suitable counterions include, for example, halides (e.g., Cl, Br, I, or F, preferably Cl, Br, or I), sulfate, and methylsulfate.

Suitable cationic polymers include, for example, copolymers of vinyl monomers having cationic amine or quaternary ammonium functionalities with water-soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The cationic amines may be primary, secondary, or tertiary amines, depending upon the particular species and the pH of the composition. In general, secondary and tertiary amines, especially tertiary amines, are preferred. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

Amine-substituted vinyl monomers may be polymerized in the amine form, and then optionally may be converted to ammonium by a quaternization reaction. Amines may also be similarly quaternized subsequent to formation of the polymer. For example, tertiary amine functionalities may be quaternized by reaction with a salt of the formula R'X wherein R' is a short chain alkyl, preferably a $C_1$–$C_7$ alkyl, more preferably a $C_1$–$C_3$ alkyl, and $X^-$ is an anion which forms a water-soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers useful herein may comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively, and mineral acid salts of amino-alkyl esters of homo- and co-polymers of unsaturated carboxylic acids having from 3 to 5 carbon atoms, as described in U.S. Pat. No. 4,009,256 issued to Nowack, et. al., on Feb. 22, 1977.

Other useful cationic polymers include cationic polysaccharide polymers, such as cationic cellulose derivatives and cationic starch derivatives. Cationic polysaccharide polymer materials suitable for use herein include those of the formula:

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and $X^-$ is an anionic counterion, as previously described.

Cationic cellulose is available from Amerchol Corp. (Edison, N.J., USA) In their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200®.

Other cationic polymers that may be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

4. Anti-Microbial Agent

Anti-microbial agents useful as encompassed material include those useful as cosmetic biocides and antidandruff agents including: water-soluble components such as piroctone olamine, water insoluble components such as 3,4,4'-trichlorocarbanilide(trichlosan), triclocarban and zinc pyrithione.

5. Herbal Extract

The compositions of the present invention may contain herbal extracts, including both water-soluble and water-insoluble herbal extracts. Useful herbal extracts herein include: *Polygonatum multiflori* extract, *Houttuynia cordate* extract, Phellodendron Bark extract, melilot extract, white dead nettle extract, licorice root extract, herbaceous peony extract, soapwort extract, dishcloth gourd extract, cinchona extract, creeping saxifrage extract, *Sophora angustifolia* extract, candock extract, common fennel extract, primrose extract, rose extract, *Rehmannia glutinosa* extract, lemon extract, shikon extract, alloe extract, iris bulb extract, eucalyptus extract, field horsetail extract, sage extract, thyme extract, tea extract, laver extract, cucumber extract, dove extract, raspberry extract, melissa extract, ginseng extract, carrot extract, horse chestnut extract, peach extract, peach leaf extract, mulberry extract, cornflower extract, hamamelis extract, placenta extract, thymus extract, silk extract, algae extract, althea extract, angelica dahurica extract, apple extract, apricot kernel extract, amica extract, *Artemisia capillaris* extract, astragal extract, balm mint extract, perilla extract, birch bark extract, bitter orange peel extract, Theasinensis extract, burdock root extract, burnet extract, butcherbroom extract, *Stephania cepharantha* extract, matricaria extract, chrysanthemum flower extract, citrus unshiu peel extract, cnidium extract, coix seed extract, coltsfoot extract, comfrey leaf extract, crataegus extract, evening primrose oil, gambir extract, ganoderma extract, gardenia extract, gentian extract, geranium extract, ginkgo extract, grape leaf extract, crataegus extract, henna extract, honeysuckle extract, honeysuckle flower extract, hoelen extract, hops extract, horsetail extract, hydrangea extract, hypericum extract, isodonis extract, ivy extract, Japanese angelica extract, Japanese coptis extract, juniper extract, jujube extract, lady's mantle extract, lavender extract, lettuce extract, licorice extract, linden extract, lithospermum extract, Soquat extract, luffa extract, malloti extract, mallow extract, calendula extract, moutan bark extract, mistletoe extract, mukurossi extract, mugwort extract, mulberry root extract, nettle extract, nutmeg extract, orange extract, parsley extract, hydrolyzed conchiorin protein, peony root extract, peppermint extract, philodendron extract, pine cone extract, platycodon extract, polygonatum extract, rehmannia extract, rice bran extract, rhubarb extract, rose fruit extract, rosemary extract, royal jelly extract, safflower extract, saffron crocus extract, sambucus extract, saponaria extract, *Sasa albo marginata* extract, *Saxifraga stolonifera* extract, scutellaria root extract, *Corlinellus shiitake* extract, lithospermum extract, sophora extract, laurel extract, calamus root extract, swertia extract, thyme extract, linden extract, tomato extract, turmeric extract, uncaria extract, watercress extract, logwood extract, grape extract, white lily extract, rose hips extract, wild thyme extract, witch hazel extract, yarrow extract, yeast extract, yucca extract, zanthoxylum extract, and mixtures thereof.

Commercially available herbal extracts useful herein include *Polygonatum multiflori* extracts which are water-soluble, and available from Institute of Occupational Medicine, CAPM, China National Light Industry, and Maruzen, and other herbal extracts listed above available from Maruzen.

The hair care compositions herein may further contain other additional components, which may be selected by the artisan according to the desired characteristics of the final product and which are suitable for rendering the compositions more cosmetically or aesthetically acceptable or to provide them with additional usage benefits.

Additional examples of preferred other additional components which may be formulated into the present compositions include: other conditioning agents such as hydrolysed collagen with tradename Peptein 2000 available from Hormel, panthenol available from Roche, panthenyl ethyl ether available from Roche, hydrolysed keratin, proteins, plant extracts, and nutrients; vitamins and/or amino acids, such as vitamin E with tradename Emix-d available from Eisai; surfactants such as a cationic surfactant, a nonionic surfactant, an anionic surfactant, an amphoteric surfactant, and mixtures thereof; hair-fixative polymers such as ampoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; sequestering agents, such as disodium ethylenediamine tetra-acetate; ultraviolet and infrared screening and absorbing agents, such as optical brighteners and octyl salicylate; and antidandruff agents, such as zinc pyrdinethione.

Manufacturing Process

The hair care compositions of the present invention may be formed by processes known in the art. Typically, the polypropylene glycol, the ester oil, and the gel matrix are combined in a large-scale batch or continuous mixing apparatus, heated, mixed together and/or homogenized, and then cooled to room temperature for packaging and storage. Alternatively, the pentaerythritol ester oil and/or the trimethylol ester oil may be combined with the suitable carrier via any suitable mixing apparatus.

To form a highly preferred lamellar gel matrix, water is typically heated to at least about 70° C., preferably between about 80° C. and about 90° C. The cationic surfactant and the solid fatty compound are combined with the water to form a mixture. The temperature of the mixture is preferably maintained at a temperature higher than both the melting temperature of the cationic surfactant and the melting temperature of the solid fatty compound, and the entire mixture is homogenized. After mixing until no solids are observed, the mixture is gradually cooled (e.g., at a rate of about 2° C./minute) to a temperature below 60° C., preferably less than about 55° C. During this gradual cooling process, a significant viscosity increase is observed at between about 55° C. and about 75° C. This indicates the formation of a lamellar gel matrix. After the formation of this gel matrix, the polypropylene glycol is added. This is then cooled to room temperature, to form the finished hair care composition. This results in a hair care composition containing the alkyl ethoxylate which possesses significantly improved stability and excellent performance.

Alternatively, a polypropylene glycol, an ester oil, and an alkyl alkoxylate (if present) are first combined to form a premix, and then added and mixed into the already-formed gel matrix. Typically, the weight ratio of the premix to the gel matrix is from about 1:1 to about 1:99, preferably from about 1:2 to about 1:80, and more preferably from about 1:5 to about 1:50. Without intending to be limited by theory, it is believed that by adding the premix at a lower temperature which is closer to the storage temperature of the final hair care composition, phase changes during storage are minimized, viscosity is maintained, and greater stability is achieved.

Method of Use

The hair care composition of the present invention is suitable for use as, for example, hair cosmetic compositions, hair styling compositions, and hair conditioning compositions, preferably as a leave-on and/or rinse off hair conditioning composition, and more preferably as a rinse-off hair conditioning composition. These hair care compositions are used in conventional ways to provide the conditioning, styling, and/or other benefits of the present invention. Such method of use depends upon the type of composition employed but generally involves application of an effective amount of the product to the hair, which may then be rinsed from the hair (as in the case of hair rinses) or allowed to remain on the hair (as in the case of gels, lotions, and creams). "Effective amount" means an amount sufficient enough to provide the desired bulk hair reduction benefit. In general, from about 1 g to about 50 g is applied to the hair, and/or the scalp. The hair care composition may be distributed throughout the hair, typically by rubbing or massaging the hair and scalp, or the composition may be selectively applied to certain parts of the hair. For a leave-on form, the hair care composition is preferably applied to wet or damp hair prior to drying of the hair. After such hair care compositions are applied to the hair, the hair is dried and styled in accordance with the preference of the user. In the alternative, such as for a hair styling composition, it may be applied to dry hair, and the hair is then combed or styled in accordance with the preference of the user.

Image Analysis Protocol

The Image Analysis Protocol is a system and procedure which is designed to digitally measure and analyze the components of bulk hair area and flyaway hair area, which in turn form the total hair area. This protocol provides a quantifiable, repeatable method for accurately distinguishing, measuring, and comparing total hair area, flyaway hair area, and bulk hair area before and after treatment with a hair care composition. This total hair area, flyaway hair area, and bulk hair area directly correlate with total hair volume, flyaway hair volume, and bulk hair volume, respectively. The hair care compositions of the present invention provide a significant, noticeable reduction in the bulk hair area, preferably by at least about 10%, more preferably by at least about 15%, and even more preferably by at least about 25%, as measured by the method described, below.

It has been found that a reduction in bulk hair area correlates with one or more noticeable consumer-desirable benefits, such as enhanced manageability, and/or improved compatibility. For example, it is believed that reduced bulk hair area correlates with moisturized hair which is softer, more plastic, smooth, and flexible than hair which is dried out. When hair is moisturized, the bulk hair area is reduced, because the hair is better aligned with other hairs and has less space in-between the individual hairs. Moisturized hair is also easier to comb and manage.

Figure 1:
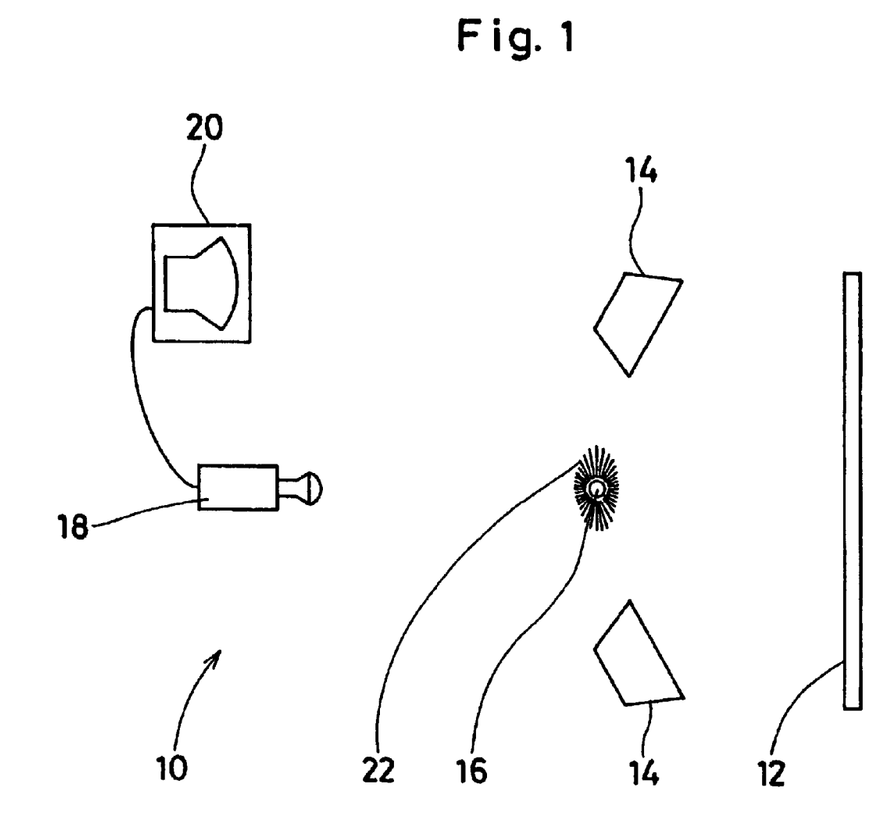
FIG. 1 is a top view of a preferred embodiment of the Image Analysis System.

Referring to the drawing, FIG. 1 shows a top view of a preferred embodiment of the Image Analysis System useful herein. The Image Analysis System, 10, consists of a white screen, 12, lighting equipment, 14, a sample holder, 16, a high-resolution digital camera, 18, and a personal computer, 20. The sample holder, 16, is placed between the white screen, 12, and the high-resolution digital camera, 18. The sample holder, 16, is typically a dip or clamp which stably suspends a hair sample, 22, about 40 cm in front of the, white screen, 12. The sample holder, 16, is typically about 80 cm from the high-resolution digital camera, 18, and positioned above the high-resolution camera's field of view, so that it is not visible in the captured images.

The white screen, 12, is a matte-finish (e.g., non-glare) white-colored screen which is illuminated to provide a constant and repeatable background against which the hair sample, 22, is measured. As the difference between bulk hair area and flyaway hair area is judged according to the brightness of the image (see below), it is important that the hair sample be photographed in front of a background which has a constant brightness. As seen in FIG. 1, the preferred lighting equipment, 14, consists of twin photography lights located on each side of the sample, and pointing towards the white screen. Each of these lights is preferably a twin florescent tube light contained within a lighting fixture, and is typically from about 20 cm to about 60 cm to the side of the sample holder, 16. This places them far enough away from the hair sample, 22, so that they are not visible by the high-resolution digital camera, 18. This assures that the captured image will only include the image of the hair sample, 22, and will not include, for example, the back-side of the lighting equipment, 14. Therefore, the lighting equipment, 14, should not interfere with or block the picture to be taken. Also, in such a configuration, the hair sample, 22, is not directly illuminated by the lighting equipment, 14. Instead, light is first reflected from the white screen, 12, and then passes through the hair sample, 22, in order to reach the high-resolution digital camera, 18. The high-resolution digital camera, 18, is focused on the hair sample, 22, and not the white screen, 12. For ease of use, the high-resolution digital camera, 18, is connected to a personal computer, 20, and automatically transfers the captured image to the computer's imaging software. Such an arrangement provides a precise picture of the profile of the hair sample, 22, and avoids any glare and/or shadows which could interfere with measurement and analysis of the hair sample, 22.

Preferably, the Image Analysis System should be located away from air currents or other forces which would disturb the hair sample, and is in a controlled temperature and humidity environment, so as to ensure repeatable results. The high-resolution digital camera (e.g., Model HC-2500 3-CCD from Fujifilm Co., of Tokyo, Japan) has a resolution of at least 1280 horizontal pixels, and 1000 vertical pixels. The high-resolution digital camera is calibrated to a linear gain, so that the incremental difference between all brightness values (an 8-bit, 0–255 brightness scale) is equal. Such a calibration may be achieved via, for example, utilizing a standard gray-scale calibration cell and/or the high-resolution digital camera's internal look-uptable (LUT). For calibration purposes, the white screen (when lit with the lighting equipment) should have a brightness value of greater than about 245, preferably from about 250 to about 255.

The typical hair sample consists of 15 cm (5 g) straight black Asian hair switches (available from Kawamuraya Co., Osaka, Japan) or straight brown Caucasian hair switches (available from International Hair Importers & products Inc., Bellerose, N.Y., U.S.A.). Straight black Asian hair switches are preferred, because their contrast against the white screen is more easily observable. The measurements using the Image Analysis Protocol are significantly easier and more reproducible when black hair switches are used. However, the hair area reduction benefits, and the corresponding hair volume reduction benefits, of the present invention are applicable to all types of hair switches. Further, it has been shown that the results achieved with hair switches are comparable to the results achieved during actual use on people.

The hair sample is prepared as follows:

1) Wet hair sample with warm water (38° C.) for 30 seconds.
2) Apply 1 ml of ammonium lauryl sulfate solution to the hair sample and lather for 30 seconds.
3) Rinse the hair sample for 60 seconds.
4) Soak the hair sample in warm water for 24 hours.
5) Apply 1 ml of ammonium lauryl sulfate solution to the hair sample and lather for 30 seconds.
6) Rinse the hair sample for 30 seconds.
7) Apply 1 ml of ammonium lauryl sulfate solution to the hair sample and lather for 30 seconds.
8) Rinse the hair sample for 60 seconds.
9) For a treated hair sample: apply 1 ml of a hair care composition to be tested to the hair sample.
10) For a treated hair sample: rinse off the hair sample for 10 seconds.
11) Comb through the front of the hair sample 5 times.
12) Comb through the back of the hair sample 5 times.
13) Squeeze off excess water from the hair sample and make the cross-section round.
14) Leave the hair sample in a 21° C./65% relative humidity room and dry for 24 hours.
15) The hair sample is then ready to be measured by the Image Analysis System.

Steps 9 and 10 are only performed for the treated hair samples. To compare the effect of a hair care composition on the bulk hair area, flyaway hair area, and total hair area, an "untreated picture" is first taken of a hair sample, and then a "treated picture" is taken. The untreated and treated bulk hair areas, flyaway hair areas, and total hair areas shown in the pictures, are then compared. Typically, the same hair switch is first used for the untreated hair sample, and then used for the treated hair sample, according to the procedure described above. Using the same hair switch minimizes sample-to-sample variations.

Once a hair sample (either treated, or untreated), 22, is prepared, it is placed on the sample holder, 16, in front of the white screen, 12. The distance from the high-resolution digital camera, 18, and the hair sample, 22, should be the same for both the untreated and treated pictures. For both the untreated and treated pictures, the hair sample is aligned so that the widest profile (according to the bottom end of the hair sample) is captured by the high-resolution digital camera. This alignment approximates the way hair is arranged on the head, and therefore provides the most accurate view of the effect on hair area (and therefore hair volume), after treatment. This also assures an accurate measurement of the bulk hair area reduction, flyaway hair area reduction, and/or total hair area reduction effects.

Once the hair is essentially motionless, an 8-bit, gray-scale picture is taken with the high-resolution digital camera, 18. Typically, the high-resolution digital camera, 18, assigns each pixel a brightness value of from 0 (pure black) to 255 (pure white). The picture is then transferred to the personal computer, 20. Alternatively, but less preferably, the personal computer may assign each pixel a brightness value from 0 to 255. Such a picture is also referred to as a "captured image," and may be saved electronically as, for example, a TIFF (Tagged Image File Format) file, for future reference. In the captured image, each hair sample appears as gray-to-black on a white background. The imaging software (e.g., Optimas v. 6.2, available from Media Cybernetics of Silver Springs, Md., U.S.A.) then analyzes the captured image, pixel-by-pixel. The imaging software uses the brightness value assigned to each pixel by the camera to classify each pixel as either black (brightness value=0–120), gray (brightness value=121–235), or white (brightness value=236–255). The imaging software then defines "bulk hair" in the captured image as the largest continuous region bounded by black lines. The "flyaway hair" is defined as black, gray, and white regions bounded by one or more gray lines, excluding the bulk hair. The term "bounded" as used herein with respect to the Imaging software indicates that the referred-to-area is completely surrounded by at least one line of the specified shade.

The imaging software then calculates the area of each region, typically in cm$^2$, to find the bulk hair area and the flyaway hair area. The total hair area is the sum of the bulk hair area and the flyaway hair area. Thus, the bulk hair area and/or the flyaway hair area may also be calculated as a percentage of the total hair area. In a preferred embodiment, the imaging software automatically sets the untreated total hair area equal to a value of 1.0, and normalizes the other values, accordingly. The imaging software may also outline and/or color code the bulk hair area and/or flyaway hair area for easy reference.

The reduction in hair volume after treatment is based on comparing the data obtained from analyzing the treated and untreated hair samples. The hair areas are calculated for the untreated total hair area (UTA), the untreated bulk hair area (UBA), and the untreated flyaway hair area (UFA). These are then compared to the calculated hair areas for the treated total hair area (TTA), the treated bulk hair area (TBA), and the treated flyaway hair area (TFA). The reduction in bulk hair area after treatment corresponds to a reduction in the bulk hair volume, and is calculated according to the following equation:

bulk hair area reduction=100*[1−(TBA/UBA)].

Similarly, the percent reduction in flyaway hair area after treatment corresponds to a reduction in the flyaway hair volume, and is calculated according to the following equation:

flyaway hair area reduction=100*[1−(TFA/UFA)].

The percent reduction in total hair area after treatment corresponds to a reduction in the total hair volume, and calculated according to the following equation:

total hair area reduction=100*[1−(TTA/UTA)].

A given hair care composition (or control) is typically tested on at least three separate hair samples. The bulk hair area reduction, flyaway hair area reduction, and total hair area reduction are then calculated for each hair sample, and an average bulk hair area reduction, average flyaway hair area reduction, and average total hair area reduction are calculated.

In a preferred embodiment of the Image Analysis Protocol, two pictures of each treated and untreated hair sample are taken. The first picture corresponds to the widest profile of the hair sample, while the second picture corresponds to the most narrow profile of the hair sample, which is typically a 90° rotation from the widest profile. Then, average values are calculated for the untreated bulk hair area, treated bulk hair area, etc. These average values are then employed in the above equations. Such a procedure is especially useful with hair samples which are slightly curved, due to their natural contours, or because of washing.

Examples of the invention are set forth hereinafter by way of illustration and are not intended to be in any way limiting of the invention, as many variations thereof are possible without departing from the spirit and scope of the invention. Ingredients are identified by chemical or CTFA name, or otherwise defined below.

EXAMPLE 1

A hair conditioning composition is formed by the following process. All percentages are by weight of the final hair care composition.

The suitable carrier is a lamellar gel matrix, which is formed as follows (all percentages are by weight of the final hair conditioning composition): about 78% deionized water is heated to 85° C., and 2% Stearamidopropyidimethylamine, available from Nikko Chemical (Tokyo, Japan) is mixed together with 2.5% cetyl alcohol and 4.5% stearyl alcohol from Shin-nihon Rika (Tokyo, Japan), and 0.64% L-glutamic acid from Ajinomoto (Osaka, Japan). The aqueous carrier is maintained at a temperature of about 85° C. for about 5 minutes with continuous mixing, until the components are homogenized, and no solids are observed. The aqueous carrier is then gradually cooled to about 55° C. and maintained at this temperature, until a lamellar gel matrix forms. 5% ester oil (caprylic/capric triglyceride under trade name Miglyol812 available from Degussa-Hüls AG of Frankfurt, Germany) and 1% pentaerythritol tetraisostearate (KAK P.T.I. available from Koukyu Alcohol Kogyo Co. of Chiba Prefecture, Japan) are also added to the lamellar gel matrix.

5% PPG-34 (New Pol PP-2000 available from Sanyo Kasei, Osaka, Japan; weight average molecular weight=2, 000 g/mol) is mixed with the lamellar gel matrix with constant stirring for 15 minutes, to assure homogenization. A perfume, a preservative, and the remaining ingredients are also added to the hair care composition. The lamellar gel matrix is maintained at about 55° C. during this time. After it is homogenized, it is allowed to cool to room temperature, packaged, and stored.

This hair conditioning composition is suitable for use as either a rinse-off, or leave-on form. When normally applied and used, this hair conditioning composition also provides a noticeable reduction in bulk hair area and total hair area.

EXAMPLE 2

The following example is representative of the benefits of the present invention. Example 2, a rinse-off hair conditioning composition of the present invention was prepared according to the method described in Example 1.

|  | EXAMPLE 2 |
|---|---|
| Cetyl Alcohol | 2.857 |
| Stearyl Alcohol | 5.143 |
| Stearamidopropyldim thylamine | 2.000 |

|  | EXAMPLE 2 |
| --- | --- |
| L-Glutamic Acid | 0.640 |
| PPG-34 | 5.000 |
| Miglyol 812 | 5.000 |
| Pentaerythritol tetraisostearat | 1.000 |
| Water, minors | balance |
| Viscosity (cps) | 23900 |
| Volume data (vs. Untreated) |  |
| Bulk hair area reduction % | 29 |
| Flyaway hair area reduction % | 32 |
| Total hair area reduction % | 30 |

Example 2 provides a significant reduction in bulk hair area, flyaway hair area, and total hair area.

EXAMPLE 3

The following hair conditioning compositions having a lamellar gel matrix are formed by the process described in Example 1:

| Component | A | B | C | D | E |
| --- | --- | --- | --- | --- | --- |
| PPG-34 *1 | 5.0 | — | — | — | 2.0 |
| Polypropylene glycol *2 | — | 3.0 | — | — | 1.0 |
| Polyoxypropylene qlyceryl ether *3 | — | — | 4.0 | — | — |
| Polyoxypropylene sorbitol *4 | — | — | — | 5.0 | — |
| PPG-10 butanediol *5 | — | — | — | 2.0 | 1.0 |
| Cetyl hydroxyethyl cellulose *6 | 0.25 | — | — | — | 0.25 |
| Oleyl alcohol *7 | — | — | — | 1.0 | — |
| Caprylic/capric triglyceride *8 | 5.0 | 5.0 | 3.0 | 5.0 | 5.0 |
| Pentaerythritol tetraisostearate *9 | 1.0 | 1.0 | 1.0 | — | 7.5 |
| Mineral oil *10 | — | — | 1.0 | — | 1.0 |
| Stearamidopropyldimethylamine *11 | 2.0 | 2.0 | — | — | 1.0 |
| L-Glutamic acid | 0.6 | — | — | — | 0.3 |
| Lactic acid | — | 1.0 | — | — | — |
| Behentrimonium chloride *12 | — | — | 2.0 | — | — |
| Stearyltrimonium chloride *13 | — | — | — | 2.0 | — |
| Cetrimonium chloride *14 | — | — | — | — | 1.0 |
| Distearyldimonium chloride *15 | — | — | — | 2.0 | — |
| Cetyl alcohol *16 | 2.5 | 2.4 | 5.6 | 1.8 | 2.0 | 3.0 |
| Stearyl alcohol *17 | 4.5 | 3.6 | — | 2.7 | 4.0 | 5.0 |
| Cyclomethicone & Dimethicone *18 | 4.0 | — | 8.0 | 3.0 | 4.0 | 2.0 |
| Dimethicone/Dimethiconol *19 | — | 1.0 | — | — | — | 2.0 |
| Cyclomethicone/Dimethiconol *20 | — | — | — | 2.0 | — | — |
| Hexylene Glycol | — | — | — | — | 2.0 | — |
| Polyethylene Glycol 200 *21 | — | 1.0 | — | — | — | 1.0 |
| 2,4-dimethoxy-6-(1'pyrenyl)-1,3,5-triazine *22 | — | — | — | — | — | 0.5 |
| Porphyrin *23 | — | — | — | — | 0.5 | — |
| Benzophenone-4 *24 | — | — | 0.2 | — | — | — |
| Octyl Methoxycinnamate *25 | — | 0.1 | — | 1.0 | — | — |
| Vitamin E | — | — | — | — | 0.05 | — |
| Panthenol *26 | 0.1 | — | — | — | — | — |
| Methyl Paraben | 0.2 | 0.2 | 0.2 | 0.2 | 0.2 | 0.2 |
| Phenoxyethanol | 0.3 | 0.3 | 0.3 | 0.3 | 0.3 | 0.3 |
| EDTA | 0.2 | 0.1 | — | — | 0.1 | 0.2 |
| Disodium EDTA | — | 0.1 | 0.1 | 0.2 | 0.1 | — |
| Benzyl alcohol | 0.4 | 0.4 | 0.5 | 0.4 | 0.2 | 0.40 |
| Perfume | 02 | 0.1 | 0.2 | 0.2 | 0.20 | 0.2 |
| Deionized Water | q.s. to 100% |

Definitions of Components
*1 New Pol PP-2000 available from Sanyo Kasei
*2 New Pol PP-4000 available from Sanyo Kasei, weight average molecular weight = 4000.
*3 New Pol GP-4000 available from Sanyo Kasei
*4 New Pol SP-4000 available from Sanyo Kasei
*5 Probutyl DB-10 available from Croda, Inc.
*6 NATROSOL PLUS 330CS from Aqualon Co., Delaware, USA.
*7 UNJECOL 90BHR available from Shin-nihon Rika
*8 Miglyol812 available from Degussa-Huls AG

| Component | A | B | C | D | E |
| --- | --- | --- | --- | --- | --- |

*9 KAK P.T.I. available from Koukyu Alcohol Kogyo Co. of Chiba Prefecture, Japan
*10 BENOL available from Witco Chemicals, Greenwich, Connecticut, USA
*11 available from Nikko Chemical, Tokyo, Japan
*12 Varisoft BT85 available from Witco Chemicals
*13 Varisoft TSC available from Witco Chemicals
*14 Varisoft CTB40 available from Witco Chemicals
*15 Varisoft TA100 available from Witco Chemicals
*16 KONOL series available from Shin-nihon Rika
*17 KONOL series available from Shin-nihon Rika
*18 85%/15% mixture of D5 cyclomethicone and dimethicone gum (weight molecular weight of about 400,000 to about 600,000) from General Electric Co.
*19 DCQ2-1403 available from Dow Corning
*20 DCQ2-1401 available from Dow Corning
*21 Carbowax PEG200 available from Union Carbide
*22 available from Ciba Geigy
*23 available from Wako Chemical, Osaka, Japan
*24 Uvnul MS-40 available from BASF
*25 Parasol MCX available from Roche
*26 available from Roche

EXAMPLE 4

A hair care composition is formed by the following process. All percentages are by weight of the final hair care composition.

About 2% polyoxypropylene glyceryl ether (trade name New Pol GP-4000 available from Sanyo Kasei, Osaka, Japan) is mixed with an aqueous carrier [95% deionized water, 0.5% acrylic acid/alkyl acrylate copolymer 1 (tradename PEMULEN TR-1 available from B. F. Goodrich, Cleveland, Ohio, U.S.A.), 0.2% Laureth-12 (Nikko Chemical, Tokyo, Japan), and 0.5% dimethicone and Dimethiconol (tradename DCQ2-1403 available from Dow Corning, Midland, Mich., U.S.A.)], at a temperature of 35° C. 1% trimethylol propane trioleate (KAK T.T.I. available from Koukyu Alcohol Kogyo Co. of Chiba Prefecture, Japan) is added. A perfume, a preservative, and the remaining minor ingredients are also added to the hair care composition.

The hair care composition formed possesses significantly improved stability of the alkyl ethoxylate, and/or improved deposition efficiency, even though the suitable carrier is not a gel matrix. When applied to hair as a hair lotion composition, and the hair is dried, a significant, noticeable reduction in bulk hair area and total hair area is observed.

EXAMPLE 5

The following hair care compositions are formed by the process described herein:

TABLE I

| | A | B | C | D | E | F |
| --- | --- | --- | --- | --- | --- | --- |
| PPG-34 *1 | 5.0 | — | — | — | — | 2.0 |
| Polypropylene glycol *2 | — | 3.0 | — | — | — | 1.0 |
| Polyoxyproplene glyceryl ether *3 | — | — | 4.0 | — | — | — |
| Polyoxypropylene sorbitol *4 | — | — | — | 5.0 | — | — |
| PPG-10 butanediol *5 | — | — | — | — | 2.0 | 1.0 |
| Oleyl alcohol *6 | 1.0 | — | — | — | — | — |
| Caprylic/capric triglyceride *7 | — | — | 1.0 | 0.5 | — | — |
| Trimethylol propane trioleate *8 | — | 2.0 | — | 1.0 | — | 1.5 |
| Pentaerythritol tetraisostearate *9 | 1.0 | — | 2.0 | — | 2.5 | — |
| Mineral oil *10 | — | — | — | — | — | 1.0 |
| Carbomer 1 *11 | 0.1 | — | 0.2 | — | 0.1 | — |

TABLE I-continued

|  | A | B | C | D | E | F |
|---|---|---|---|---|---|---|
| Carbomer 2 *12 | — | — | — | 0.5 | — | 0.3 |
| Triethanolamine *13 | 0.5 | 0.6 | 0.7 | 0.6 | 0.5 | 0.5 |
| Dimethicone/Dimethiconol *14 | 1.0 | 1.0 | — | — | — | 2.0 |
| Cyclomethicone/Dimethiconol *15 | — | — | — | 2.0 | — | — |
| Cyclomethicone/Dimethicone *16 | — | — | 2.0 | — | 2.0 | — |
| Cyclomethicone *17 | — | — | 1.0 | — | — | — |
| Polyquaternium-39 *18 | 0.2 | 0.1 | — | — | — | — |
| Hexylene Glycol | — | — | — | — | 2.0 | — |
| Polyethylene Glycol 200 *19 | — | 2.0 | — | — | — | 1.0 |
| 2,4-dimethoxy-6-(1'pyrenyl)-1,3,5-triazine *20 | — | — | — | — | — | 1.0 |
| Porphyrin *21 | — | — | — | — | 1.0 | — |
| Benzophenone-4 *22 | 0.1 | — | 0.2 | — | — | — |
| Octyl Methoxycinnamate *23 | — | 0.1 | — | 1.0 | — | — |
| Vitamin E | — | — | — | — | 0.05 | — |
| Panthenol *24 | 0.1 | — | — | — | — | — |
| Methyl Paraben | 0.2 | 0.2 | 0.2 | 0.2 | 0.2 | 0.2 |
| Phenoxyethanol | 0.3 | 0.3 | 0.3 | 0.3 | 0.3 | 0.3 |
| Disodium EDTA | 0.1 | 0.1 | 0.1 | 0.1 | 0.1 | 0.1 |
| Perfume solution | 0.1 | 0.1 | 0.1 | 0.1 | 0.1 | 0.1 |
| Deionized Water | q.s. to 100% | | | | | |

Definitions of Components
*1 New Pol PP-2000 available from Sanyo Kasei
*2 New Pol PP-4000 available from Sanyo Kesei, weight average molecular weight = 4000.
*3 New Pol GP-4000 available from Sanyo Kasei
*4 New Pol SP-4000 available from Sanyo Kas i
*5 Probutyl DB-10 available from Croda, Inc.
*6 UNJECOL 90BHR available from Shin-nihon Rika
*7 Miglyol812 available from Degussa-Hüls AG
*8 KAK T.T.I. available from Koukyu Alcohol Kogyo Co. of Chiba Prefecture, Japan
*9 KAK P.T.I. available from Koukyu Alcohol Kogyo Co.
*10 BENOL available from Witco Chemicals
*11 Carbopol 981 available from B.F. Goodrich
*12 Carbopol Ultrez 10 available from B.F. Goodrich
*13 available from Nippon Shokubai
*14 DCQ2-1403 available from Dow Corning
*15 DCQ2-1401 available from Dow Corning
*16 Gum/Cyclomethicone blend available from Shin-Etsu
*17 DC345 available from Dow Corning
*18 Merquat 3330 available from Calgon, Co., Pittsburgh, Pennsylvania, USA.
*19 Carbowax PEG200 available from Union Carbide
*20 available from Ciba Geigy
*21 available from Wako Chemical, Osaka, Japan
*22 Uvnul MS-40 available from BASF
*23 Parasol MCX available from Roche
*24 available from Roche

What is claimed is:

1. A rinse-off hair care composition comprising, by weight of the hair care composition:

A. from about 0.5% to about 10%, by weight, of a polypropylene glycol having a weight average molecular weight of from about 1,000 g/mol to about 60,000 g/mol, the polypropylene glycol being selected from the group consisting of a single-polypropylene glycol-chain segment polymer, a multi-polypropylene glycol-chain segment polymer, and mixtures thereof, and wherein the polypropylene glycol has a solubility in water at 25° C. of less than about 1 g/100 g water, wherein the single-polypropylene glycol-chain segment polymer has the formula:

(Formula I), wherein a is a value from about 4 to about 400, and wherein the multi-polypropylene glycol-chain segment polymer has the formula:

(Formula II), wherein n is a value from about 0 to about 10, wherein each R is independently selected from the group consisting of H, and $C_1$–$C_{30}$ alkyl, wherein each b is independently a value from 0 to 2, wherein c and d are independently a value from 0 to 2, wherein b+c+d is at least 2, wherein each e is independently a value of 0 or 1, and wherein each x, y, and z is independently a value of from about 1 to about 120;

B. from about 0.5% to about 10% of an ester oil of the formula:

(Formula V), wherein each $R^1$ is independently a $C_1$–$C_{22}$ alkyl, and wherein the HLB value of the ester oil is less than about 4;

C. from about 60% to about 99% of a gel matrix comprising a cationic surfactant, a solid fatty compound, and water, wherein the weight ratio of cationic surfactant to solid fatty compound is from about 1:1 to about 1.20; and D. the balance being other additional components, wherein the viscosity of the hair care composition is from about 5,000 cps to about 40,000 cps, wherein the hair care composition is a rinse-off hair conditioning composition.

2. The rinse-off hair care composition of claim 1, wherein the hair care composition reduces bulk hair area by at least about 10%, according to an Image Analysis Protocol.

* * * * *